(12) United States Patent
Hansen

(10) Patent No.: US 6,662,046 B2
(45) Date of Patent: Dec. 9, 2003

(54) DEFIBRILLATOR WITH AUTOMATIC TURN ON, DEFIBRILLATOR STORAGE CASE, AND RELATED SYSTEM AND METHOD

(75) Inventor: Kim J. Hansen, Renton, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 172 days.

(21) Appl. No.: 10/034,313

(22) Filed: Dec. 21, 2001

(65) Prior Publication Data

US 2003/0120311 A1 Jun. 26, 2003

(51) Int. Cl.$^7$ ................................................. A61N 1/39
(52) U.S. Cl. ............................................................. 607/5
(58) Field of Search ........................................ 607/4–8

(56) References Cited

U.S. PATENT DOCUMENTS

| | | |
|---|---|---|
| 5,607,454 A | 3/1997 | Cameron et al. |
| 5,735,879 A | 4/1998 | Gliner et al. |
| 5,836,993 A | 11/1998 | Cole |
| 5,879,374 A | 3/1999 | Powers et al. |

*Primary Examiner*—Scott M. Getzow

(57) ABSTRACT

An automated or semi-automated defibrillator (AED) automatically turns on when an operator removes it from a storage location. This automatic activation often decreases the time it takes the operator—particularly an inexperienced or anxious operator—to set up and use the AED to resuscitate a patient in cardiac arrest. Furthermore, the AED can be designed to automatically turn off when the operator returns it to the storage location.

41 Claims, 8 Drawing Sheets

DEFIBRILLATOR WITH AUTOMATIC TURN ON, DEFIBRILLATOR STORAGE CASE, AND RELATED SYSTEM AND METHOD

FIELD OF THE INVENTION

The invention relates generally to a medical device such as an automated or semi-automated external defibrillator (AED), and more particularly to a defibrillator that can turn on, turn off, or turn both on and off automatically, a case for storing the defibrillator, a system that includes the defibrillator and the case, and related methods.

BACKGROUND OF THE INVENTION

AEDs have saved the lives of many patients who have suffered cardiac arrest in non-hospital settings, and, as a result of advances in AED technology, the number of lives saved per year is rising. An AED is a battery-operated device that analyzes a patient's heart rhythm, and, if appropriate, administers an electrical shock (automated) or instructs an operator to administer an electrical shock (semi-automated) to the patient via electrode pads. For example, such a shock can often revive a patient who is experiencing ventricular fibrillation (VF).

Because cardiac arrest can cause permanent damage or death within a short time if left untreated, an AED operator should be able to set up and activate an AED within seconds after the operator arrives at the scene. Statistically, for each minute that the patient is in cardiac arrest and is not receiving cardiopulmonary resuscitation (CPR), his chance of survival decreases by 10%. And in most cases, there is no chance for resuscitation after 10 minutes. Unfortunately, many people do not know how to administer CPR. And, even in the best of circumstances, it can take a few minutes to retrieve the AED and a few additional minutes for the AED to diagnose and shock the patient. Therefore, even if the patient is discovered immediately, the operator often has little time to set up and activate the AED without further decreasing the patient's chance of survival. Clearly, the faster the operator can activate and set up the AED, the better the chances that the patient will survive.

Unfortunately, with the continued proliferation of easily accessed AEDs, it is increasingly likely that an operator will have little or no experience using a particular brand of AED and/or may panic during a resuscitation attempt, and thus may waste valuable seconds trying to figure out how to turn on, i.e., activate, an AED. Although an entity such as an airline may provide AEDs in its places of business and train its employees to operate them, an employee typically uses these AEDs so infrequently that his skills may become "rusty" even if the entity offers periodic refresher courses. Furthermore, non-employees such as airline passengers may have no formal training in the use of an AED; consequently, the first time that such a person operates an AED may be during a resuscitation attempt. Now although an AED will often "walk" an operator through the steps of resuscitation once the AED is activated, the operator typically must determine how to activate the AED on his own. Unfortunately, the operator's "rustiness" or lack of training coupled with the anxiety induced by the resuscitation effort may make it difficult for the operator to determine how to activate the AED. Furthermore, the label of the AED's on/off switch may be confusing to the operator, and thus may exacerbate his difficulty in determining how to activate the AED. For example, the on/off switch may use a "1" to indicate "on", and a "0" to indicate "off." But although "1" and "0" are touted as being "universal" on and off symbols, respectively, they are often unrecognizable to an operator without electronics or computer experience. And although the AED may use the words "on" and "off" or their non-English equivalents to label the switch, these words may be unrecognizable to an operator who speaks another language or may be difficult to see under non-optimal lighting conditions.

General Overview of an AED

FIG. 1 is a perspective view of a conventional AED system 10, which includes an AED 12 for generating a defibrillation shock and defibrillator electrode pads 14a and 14b for providing the shock to a patient (not shown). A connector 16 couples the electrode pads 14a and 14b to a receptacle 18 of the AED 12. Typically, the electrode pads 14a and 14b are sealed within a package (not shown) that an operator (hands shown in FIG. 1) tears or peels open to access the electrode pads 14a and 14b. The package acts as a moisture barrier that prevents the electrode-pad contact gel (not shown) from prematurely drying out during storage of the electrode pads 14a and 14b. A battery 19, which typically is a lithium-based battery, can provide relatively high power so that the AED 12 can quickly generate the defibrillation shock. The battery 19 and AED 12 may be stored separately, with the operator connecting the battery 19 to the AED 12 just prior to use in an emergency. Or preferably, the battery 19 and AED 12 may be stored together, with the battery 19 connected to the AED 12 during storage. For example, the battery 19 is often disposed inside of the AED 12 until it needs to be replaced.

The AED 12 includes a housing 21, a main on/off switch 20, a display 22 for displaying operator instructions, cardiac waveforms, or other information, a speaker 24 for providing audible operator instructions or other information, status light-emitting diodes (LEDs) 26, a status indicator 28, and a shock button 30, which the operator presses to deliver a shock to the patient (not shown). The AED 12 may also include a microphone 32 for recording the operator's voice and other audible sounds that occur during the rescue, and non-volatile memory such as a data card 34 for storing these sounds along with the patient's ECG and a record of AED events for later study.

Still referring to FIG. 1, during an emergency where it is determined that the patient (not shown) may need a shock, the operator retrieves the AED 12, then presses the on/off switch 22 to activate the AED 12. Once activated, the AED 12 displays instructions on the display 24 and/or "speaks" instructions via the speaker 26. Following these instructions, the operator removes the electrode pads 14a and 14b from the protective package (not shown) and inserts the connector 16 into the receptacle 18. Then, the operator places the electrode pads 14a and 14b on the patient in the respective positions shown in the pictures on the pads and on the AED 12. After the operator places the electrode pads 14a and 14b on the patient, the AED 12 analyzes the patient's ECG to determine whether the patient is suffering from a shockable heart rhythm. If the AED 12 determines that the patient is suffering from a shockable heart rhythm, then it instructs the operator to depress the shock button 30 to deliver a shock to the patient. Conversely, if the AED 12 determines that the patient is not suffering from a shockable heart rhythm, it informs the operator to seek appropriate non-shock treatment for the patient and disables the shock button 30 so that even if the operator presses the button 30, the AED 12 does not shock the patient.

As discussed above, the operator's inexperience, anxiety, and/or his inability to read the label of the switch 20 may delay the activation, and thus the set up and use, of the AED 12. Unfortunately, this delay may reduce the patient's chance of survival by increasing the time that he is in cardiac arrest.

Consequently, a need exists for an AED that activates automatically when needed to resuscitate a patient.

SUMMARY OF THE INVENTION

In one embodiment of the invention, a defibrillator includes a housing and an activator disposed or attached to the housing. The activator activates the defibrillator when the housing moves from a predetermined location.

Such a defibrillator can be designed such that it activates automatically when an operator removes it from a storage location. This automatic activation often decreases the time it takes the operator—particularly an inexperienced or anxious operator—to set up and use the AED, and thus often increases a patient's chance of survival by reducing the time that he is in cardiac arrest.

In another embodiment of the invention, a defibrillator includes a housing and a deactivator disposed or attached to the housing. The deactivator deactivates the defibrillator when the housing is disposed in a predetermined location.

Such a defibrillator can be designed such that it deactivates automatically when an operator returns it to a storage location.

In yet another embodiment of the invention, a defibrillator includes a housing and an activator/deactivator disposed or attached to the housing. The activator/deactivator activates the defibrillator when the housing moves from a predetermined location and deactivates the defibrillator when the housing is disposed in the predetermine location.

DESCRIPTION OF THE PREFERRED EMBODIMENTS

The following discussion is presented to enable a person skilled in the art to make and use the invention. Various modifications to the embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein.

Figure 1:
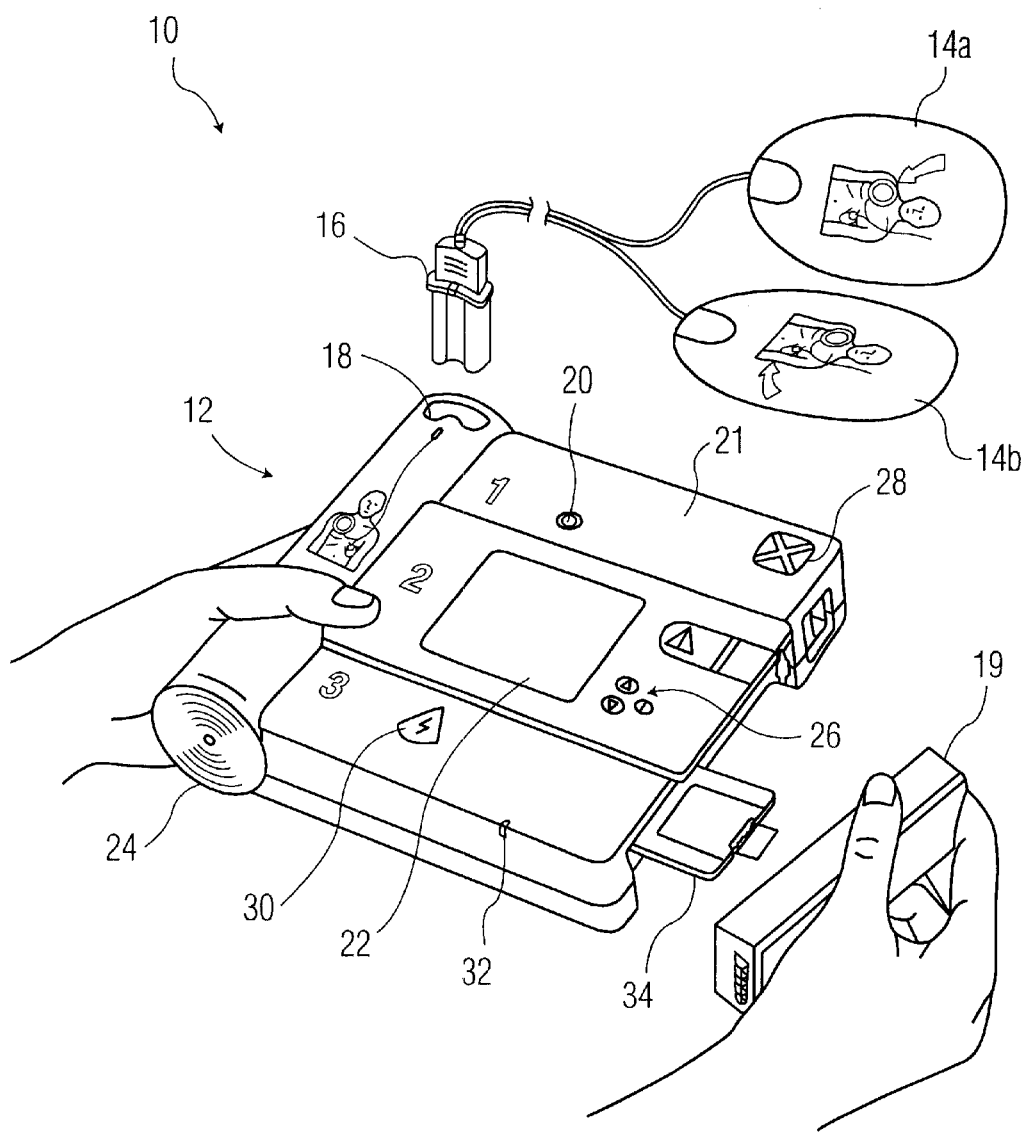
FIG. 1 is a perspective view of a conventional AED system.
Figure 2:
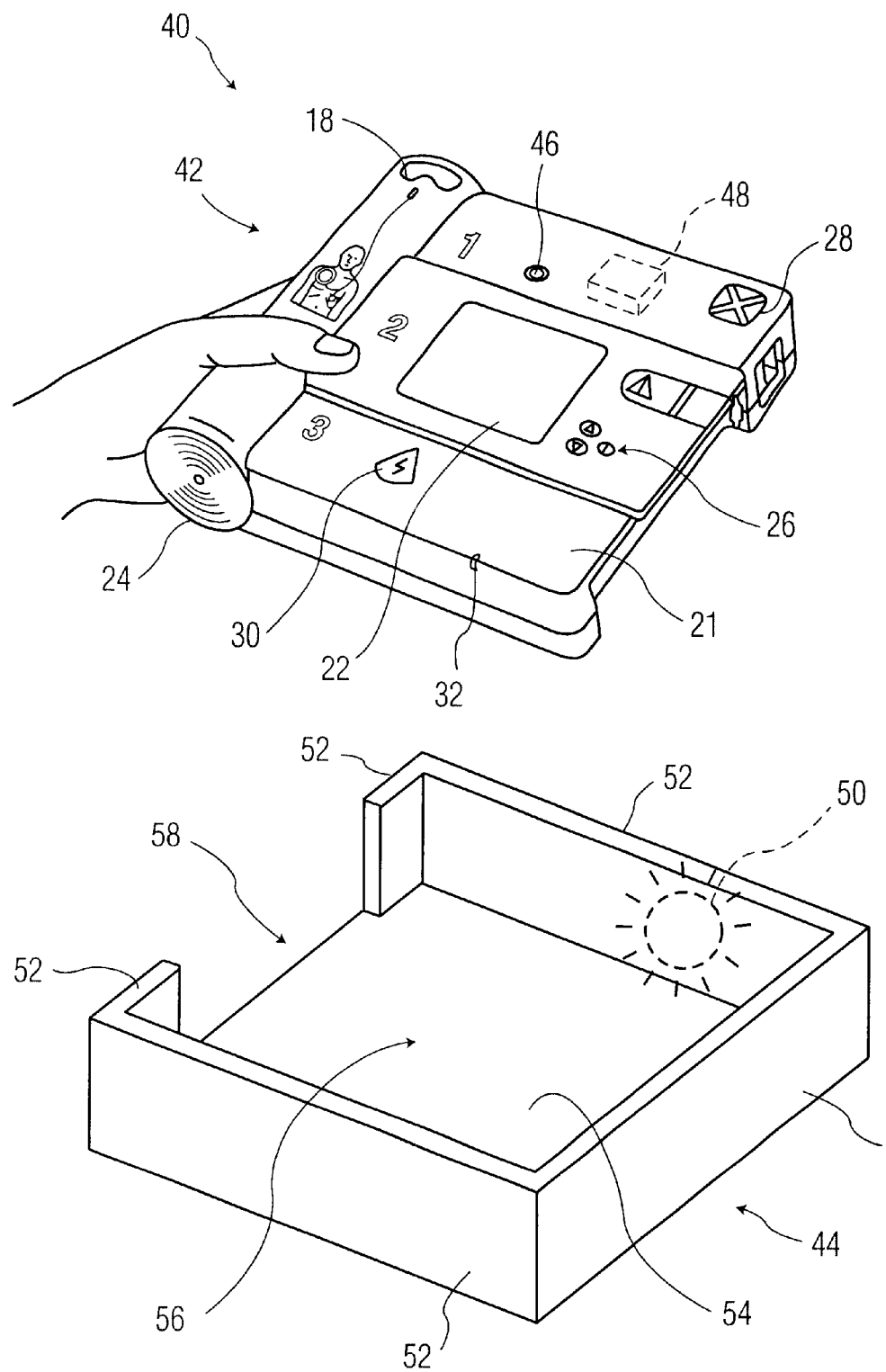
FIG. 2 is a perspective view of an AED system that includes an automatically activating/deactivating AED according to an embodiment of the invention.

FIG. 2 is a perspective view of an AED system 40 that includes an automatically activating/deactivating AED 42 and an AED storage case 44 according to an embodiment of the invention. For clarity, like numerals in FIGS. 1 and 2 refer to like elements in the systems 10 and 40, and the pads 14a and 14b are omitted from FIG. 2. The AED 42 and case 44 are constructed such that when the AED is in an automatic mode and an operator (hand shown in FIG. 2) removes the AED 42 from the case 44, the AED activates without further operator action. That is, when the AED 42 is in the automatic mode, merely removing the AED 42 from the case 44 automatically turns the AED "on". Conversely, when the AED 42 is in the automatic mode and the operator returns the AED 42 to the case 44, the AED deactivates without further operator action. That is, when the AED 42 is in the automatic mode, merely returning the AED 42 to the case 44 automatically turns the AED "off".

The AED 42 includes a manual three-position power switch 46. When the switch 46 is in its "on" and "off" positions, the AED 42 is active or inactive, respectively, regardless of its location. But when the switch 46 is in the "auto" position, the AED 42 is active while out of the case 44 and is inactive while in the case as discussed above and below.

The AED 42 also includes an activator/deactivator 48, such as a conventional Hall-effect or magnetic-reed switch circuit. When the switch 46 is in its "on" and "off" positions, the activator/deactivator 48 has no affect on the operation of the AED 42. But when the switch 46 is in its "auto" position, the activator/deactivator 48 deactivates circuitry (FIG. 9) within the AED in the presence of a magnetic field, and activates the circuitry in the absence of a magnetic field. Although the activator/deactivator 48 may be located anywhere within or on the AED 42, it is typically located near a side of the AED so that it can more easily sense a magnetic field that is generated by the case 44 as discussed below.

The storage case 44 includes a deactivator element 50, walls 52 and a back 54 that define an AED-storage compartment 56, and an opening 58 that allows the operator to grasp and remove the AED 42 from the storage compartment. The element 50, which may be a conventional magnet, generates a magnetic field that causes the activator/deactivator 48 to deactivate the AED circuitry (FIG. 9) when the AED 42 is disposed within the case 44. Although the element 50 may be located anywhere within or on the case 44, it is typically disposed within or on a wall 52 or the back 54 such that it is adjacent to the activator/deactivator 48 when the AED 42 is disposed within the case. This adjacent location allows the activator/deactivator 48 to better sense the magnetic field that the element 50 generates. Furthermore, although the walls 52 and back 54 are shown as being rigid, they may be flexible, such as where the case 44 is a zippered fabric case (not shown). Moreover, the case 44 may include conventional protrusions or other means (not shown) for securing the AED 42 within the case 44.

Still referring to FIG. 2, the operation of the system 40 in manual and automatic modes is discussed according to an embodiment of the invention.

In the manual mode, the AED 42 is stored in the case 44 with the switch 46 in the "off" position, which effectively bypasses the activator/deactivator 48. During a cardiac emergency, the operator removes the AED 42 from the case 44. Because the switch 46 is in the "off" position, the AED 42 does not turn on automatically. Therefore, the operator turns the switch 46 to the "on" position to activate the AED 42, and then sets up the AED and uses the AED to shock a patient (not shown) as discussed above in conjunction with FIG. 1. Alternatively, as discussed below, the operator may turn the switch from "off" to "auto", and, as long as the AED 42 is out of the case 44, the AED will operate as if the switch were in the "on" position. At the end of the resuscitation effort, the operator returns the switch 46 to the "off" position to maintain the AED 42 in the manual mode, or turns the switch 46 to the "auto" position (if not already this) to put the AED in the automatic mode, which is discussed below. Because the operator must turn the key from "off" to "on" or "auto" to activate the AED 42, the manual mode is intended for settings where the operator is likely to be thoroughly trained in the use of the AED system 40.

In the automatic mode, the AED 42 is stored in the case 44 with the switch 46 in the "auto" position, which allows the activator/deactivator 48 to control the on/off function of the AED.

During a cardiac emergency, the operator removes the AED 42 from the case 44. Because the switch 46 is in the "auto" position, the AED 42 turns on automatically, thus eliminating the need for the operator to manually turn the switch 46 to the "on" or "auto" position. Specifically, as the AED 42, and thus the activator/deactivator 48, moves a predetermined distance from the case 44, and thus from the element 50, the activator/deactivator senses a weakening magnetic field from the element. When the strength of this magnetic field falls below a predetermined threshold, the activator/deactivator 48 turns on the AED 42. In one embodiment, the sensitivity of the activator/deactivator 48 and the magnetic-field strength of the element 50 are chosen such that the activator/deactivator activates the AED 42 when the AED is more than an inch or two from the case 44. Once the AED 42 is activated, the operator sets up the AED and uses it to shock a patient (not shown) as discussed above in conjunction with FIG. 1.

After the operator finishes treating the patient with the AED 42, he returns it to the case 44. Because the switch 46 is in the "auto" position, the AED 42 turns off automatically, thus eliminating the need for the operator to manually turn the switch 46 to the "off" position. Specifically, as the AED 42, and thus the activator/deactivator 48, move within a predetermined distance of the case 44, and thus the element 50, the activator/deactivator senses a strengthening magnetic field from the element. When the strength of this magnetic field at the activator/deactivator 48 rises above the predetermined threshold, the activator/deactivator turns off the AED 42.

Other embodiments of the AED system 40 are contemplated as well. For example, the switch 46 may be omitted such that the AED 42 operates only in the automatic mode. Alternatively, one can program the operating mode of the AED 42 via a personal computer and interface (not shown) or via the screen 22. In such embodiments, when the AED 42 is in the automatic mode, one can attach a magnet to the AED near the activator/deactivator 48 to turn the AED off when it is out of the case 44.

Figure 3:
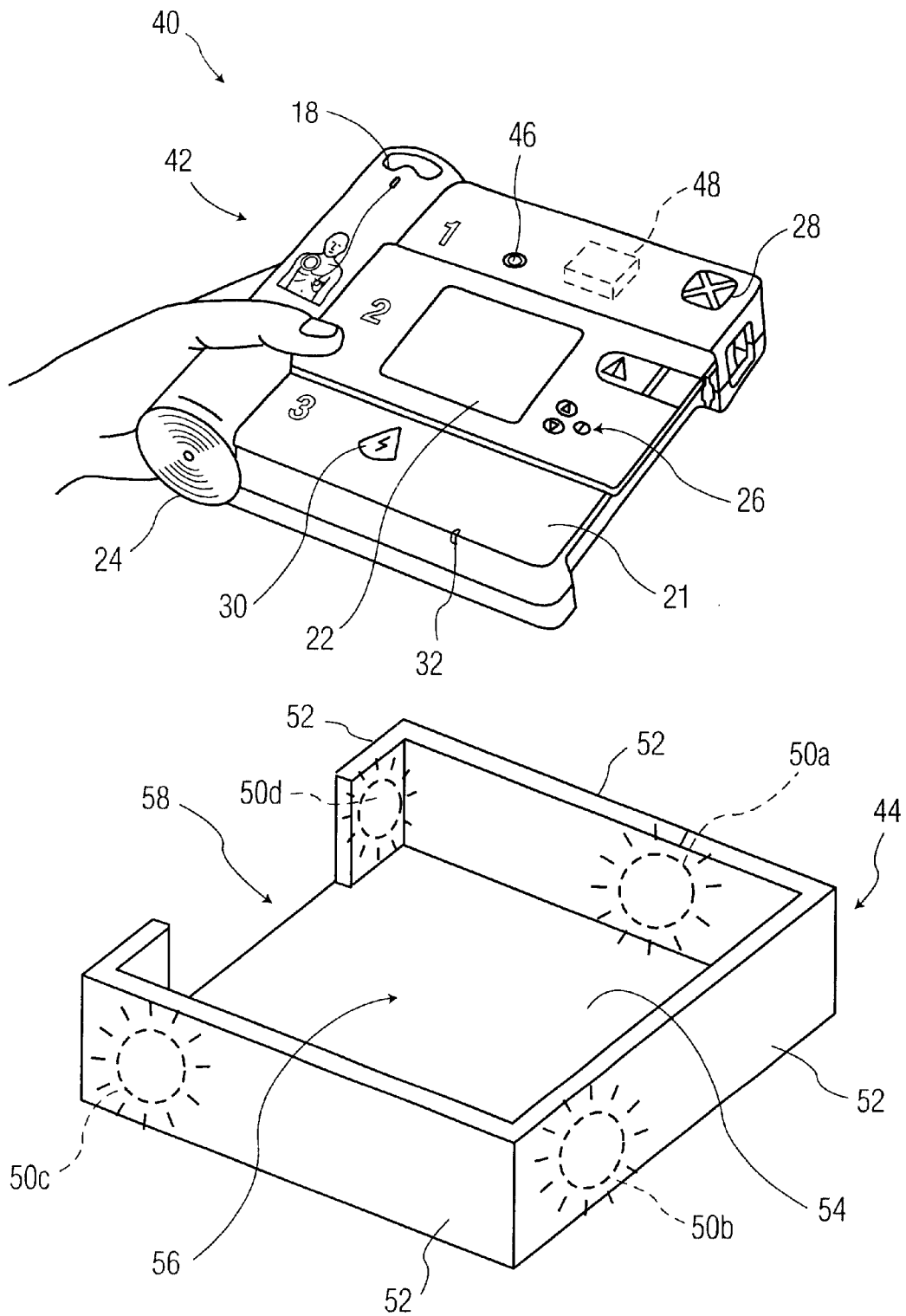
FIG. 3 is a perspective view of an alternative embodiment of the AED system of FIG. 2.

FIG. 3 is a perspective view of an alternate embodiment of the AED system 40 according to an embodiment of the invention. The AED system 40 of FIG. 3 is the same as the system 40 of FIG. 2 except that the case 44 includes multiple deactivator elements, here four elements 50a–50d. Including multiple elements 50 insures that the activator/deactivator 48 will turn off the AED 42 regardless of how the AED is positioned within the case 44. For example, the operator may place the AED 42 upside down in the case 44. But although the activator/deactivator 48 is no longer adjacent to the element 50a, it is adjacent to the element 50c. Consequently, the element 50c is close enough to cause the activator/deactivator 48 to deactivate the AED 42.

In another embodiment, the case 44 includes only one element 50, for example element 50a, that generates a magnetic field strong enough to cause the activator/deactivator 48 to deactivate the AED 42 regardless of its position within the case.

Still referring to FIG. 3, in yet another embodiment, the AED 42 includes multiple activators/deactivators 48 (only one shown in FIG. 3) that each correspond to a respective one of the elements 50. That is, each of the activators/deactivators 48 is adjacent to a respective element 50 when the AED 42 is within the case 44. The activators/deactivators 48 do not deactivate the AED 42 unless they each sense a respective magnetic field from the respective adjacent element 50. One advantage of this embodiment is that the activators/deactivators 48 will not undesirably deactivate the AED 42 in the presence of a non-case magnetic field (such as from a speaker magnet) that is strong enough or close enough for some, but not all, of the activators/deactivators to sense.

Figure 4:
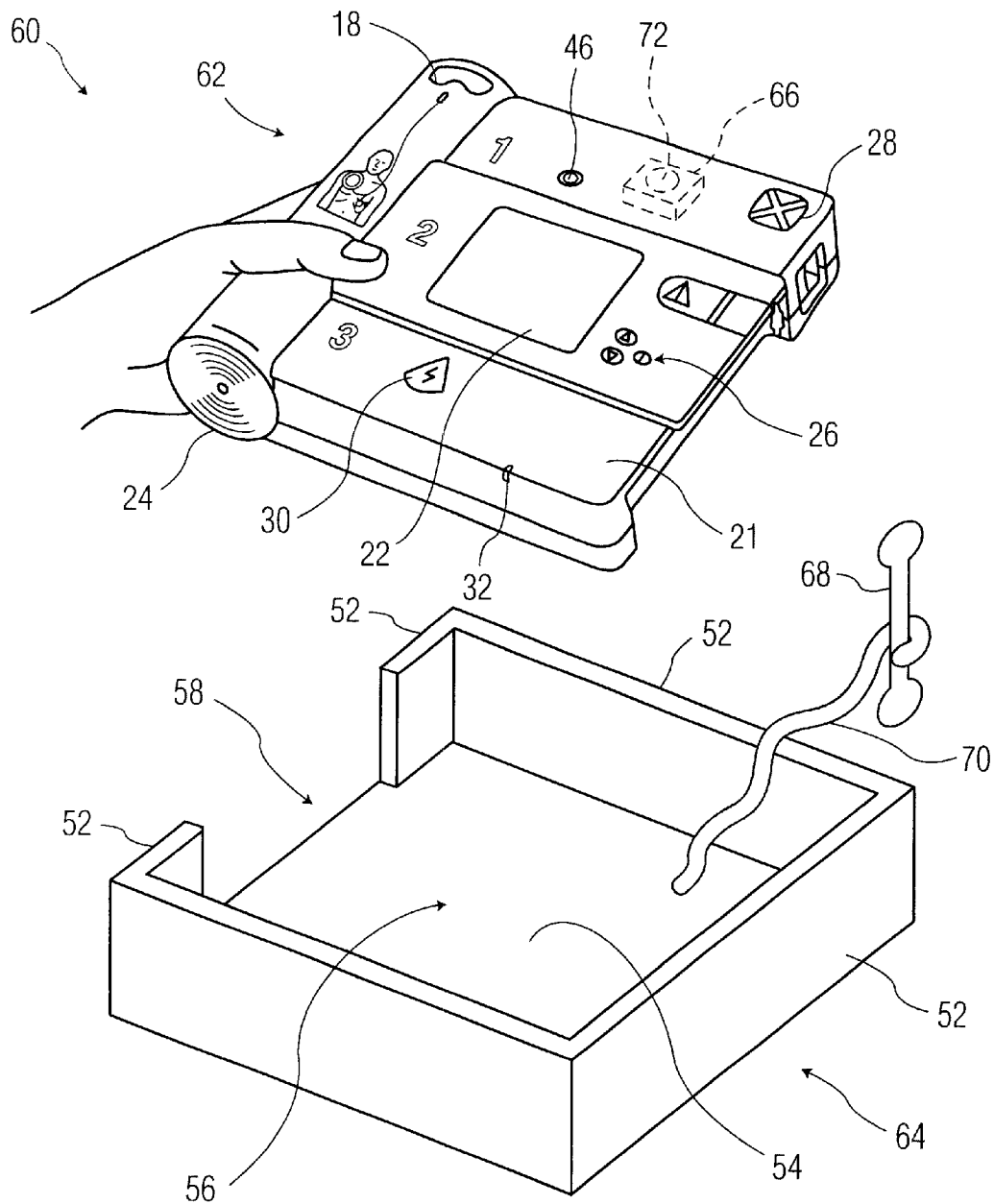
FIG. 4 is a perspective view of an AED system that includes an automatically activating/deactivating AED according to another embodiment of the invention.

FIG. 4 is a perspective view of an AED system 60 that includes an automatically activating/deactivating AED 62 and an AED storage case 64 according to another embodiment of the invention, where like numerals refer to like elements in the systems 40 (FIG. 2) and 60. The AED system 60 of FIG. 4 is the same as the system 40 of FIG. 2 except that the AED 62 includes a non-magnetic activator/deactivator switch 66 instead of the magnetic activator/deactivator 48, and the case 64 includes a non-magnetic deactivator pin 68 instead of the magnetic deactivator element 50. When the switch 46 is in the "auto" position, the switch 66 deactivates the AED 62 when the pin 68, which is tethered to the case 64 with a line 70, is disposed within a receptacle 72 of the switch. Conversely, the switch 66 activates the AED 62 when the pin 68 is not disposed within the receptacle 72.

Still referring to FIG. 4, the operation of the system 60 in the automatic mode is discussed (in the manual mode, the system 60 operates in a manner similar to that discussed above in conjunction with FIG. 2 for the system 40).

In the automatic mode, the AED 62 is stored in the case 64 with the switch 46 in the "auto" position, which allows the activator/deactivator switch 66 to control the on/off function of the AED.

During a cardiac emergency, an operator (hands shown in FIG. 4) removes the AED 62 from the case 64. Because the switch 46 is in the "auto" position, the AED 62 turns on automatically, thus eliminating the need for the operator to manually turn the switch 46 to the "on" or "auto" position. Specifically, as the AED 62 moves away from the case 64, the slack in the line 70 is taken up until the line is taut. The length of the line 70 can be any suitable value, for example between six inches and one foot. As the operator continues to move the AED 62 beyond the point where the line 70 is taut, the line effectively pulls the pin 68 out of the receptacle 72. The removal of the pin 68 causes the switch 66 to activate the AED 62. Once the AED 62 is activated, the operator sets up the AED and uses the AED to shock a patient (not shown) as discussed above in conjunction with FIG. 1.

After the operator finishes treating the patient with the AED 62, he inserts the pin 68 back into the receptacle 72 and returns the AED to the case 64. Because the switch 46 is in the "auto" position, the AED 62 turns off automatically in response to the insertion of the pin 68, thus eliminating the need for the operator to manually turn the switch 46 to the "off" position.

Other embodiments of the AED system 60 are contemplated as well. For example, the switch 46 may be omitted such that the AED 62 operates only in the automatic mode. Alternatively, one can program the operating mode of the AED 62 via a personal computer and interface (not shown) or via the screen 22. In such embodiments, when the AED 62 is in the automatic mode, one can insert a portable pin 68 into the receptacle 72 to turn the AED off when it is out of the case 64.

Figure 5:
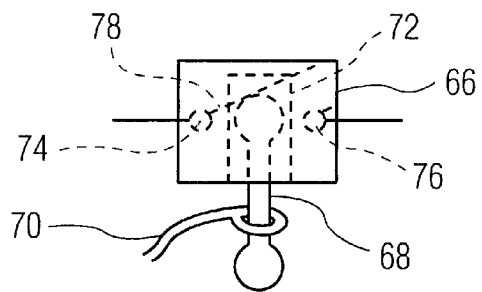
FIG. 5 is a diagram of an automatic on/off switch that can be used in the AED of FIG. 4.

FIG. 5 is a diagram of the switch 66 of FIG. 4 according to an embodiment of the invention. In addition to the receptacle 72, the switch 66 includes nodes 74 and 76 and a resilient conductor 78. When the pin 68 is disposed within the receptacle 72 as shown, the pin pushes the conductor 78 out of contact with the node 76, thus opening the switch 66. Conversely, when the pin 68 is not within the receptacle 72, the conductor 78 contacts the node 76, thus closing the switch 66.

Other embodiments of the switch 66 are contemplated. For example, the switch 66 may be an optical switch that effectively uses a beam of light (not shown) in place of the conductor 78. When the pin 68 is disposed within the receptacle 72, it breaks the beam and thus opens or closes the switch 66 depending on the switch's configuration. Conversely, when the pin 68 is not disposed within the receptacle 72, the beam is not broken, and thus the switch 66 is closed or opened depending on its configuration.

Figure 6:
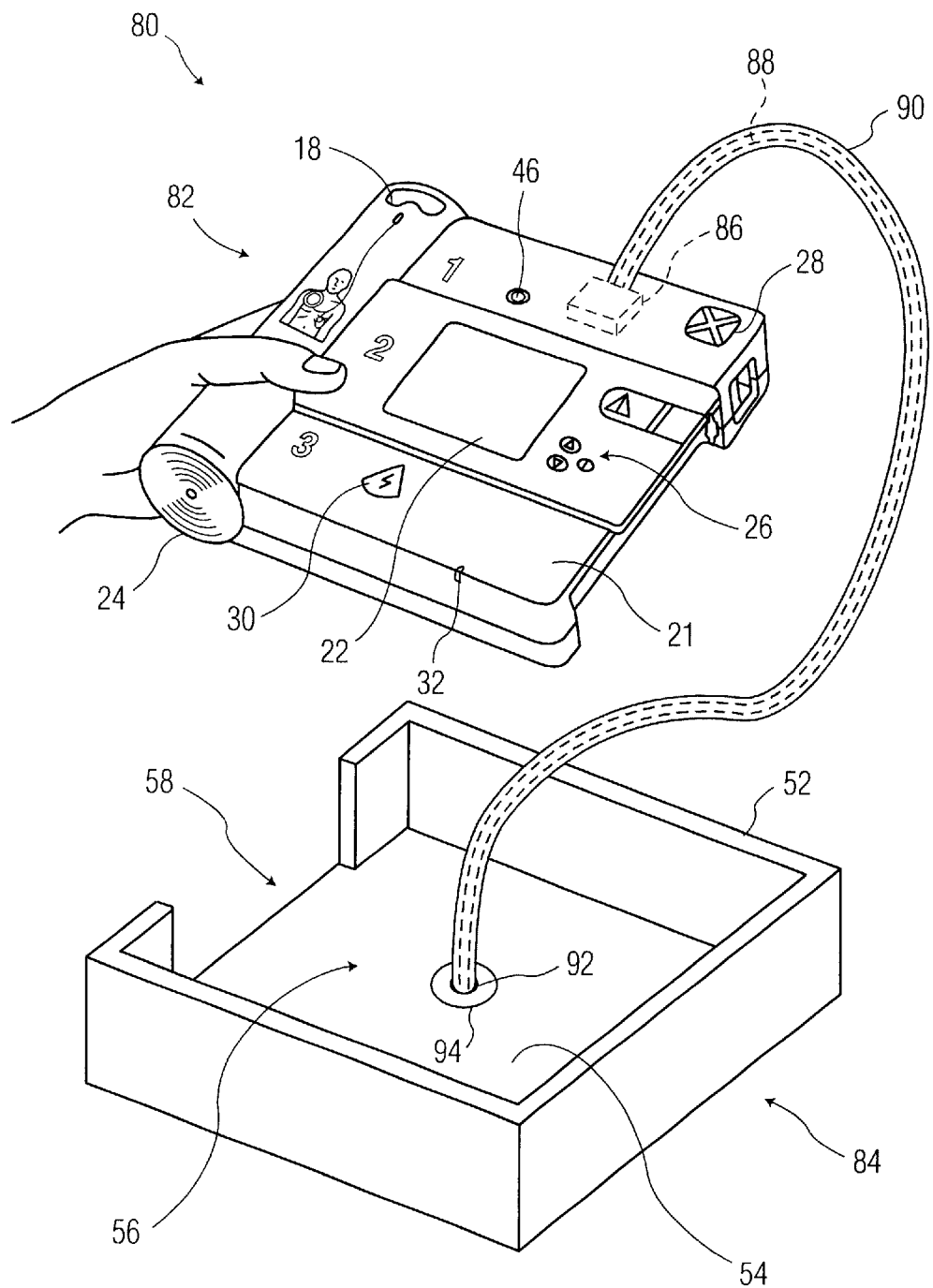
FIG. 6 is a perspective view of an AED system that includes an automatically activating/deactivating AED according to another embodiment of the invention.

FIG. 6 is a perspective view of an AED system 80 that includes an automatically activating/deactivating AED 82 and an AED storage case 84 according to another embodiment of the invention, where like numerals refer to like elements in the systems 60 (FIG. 4) and 80. The AED system 80 of FIG. 6 is the same as the system 60 of FIG. 4 except that the AED 82 includes a switch 86 that turns the AED 82 on or off depending upon whether a conductive loop 88 within a line 90 is open or closed. When the switch 46 is in the "auto" position, the switch 86 deactivates the AED 82 when the end 92 of the line 90 is attached to a conductive plate 94 that closes the loop 88. The end 92 may be conventionally attached to the plate 94 with, for example, Velcro® or adhesive. Conversely, the switch 86 activates the AED 82 when the end 92 of the line 90 is not attached to the plate 94, and thus the loop 88 is open.

Still referring to FIG. 6, the operation of the system 80 in the automatic mode is discussed (in the manual mode, the system 80 operates in a manner similar to that discussed above in conjunction with FIG. 2 for the system 40).

In the automatic mode, the AED 82 is stored in the case 84 with the switch 86 in the "auto" position, which allows the activator/deactivator switch 86 to control the on/off function of the AED.

During a cardiac emergency, an operator (hands shown in FIG. 6) removes the AED 82 from the case 84. Because the switch 46 is in the "auto" position, the AED 82 turns on automatically, thus eliminating the need for the operator to manually turn the switch 46 to the "on" or "auto" position. Specifically, as the AED 82 moves away from the case 84, the slack in the line 90 is taken up until the line is taut. The length of the line 90 can be any suitable value, for example between six inches and one foot. As the operator continues to move the AED 82 beyond the point where the line 90 is taut, the end 92 of the line detaches from the plate 94, thus opening the loop 88. The opening of the loop 88 causes the switch 86 to activate the AED 82. Once the AED 82 is activated, the operator sets up the AED and uses the AED to shock a patient (not shown) as discussed above in conjunction with FIG. 1.

After the operator finishes treating the patient with the AED 82, he reattaches the end 92 of the line 90 to the plate 94 and returns the AED to the case 84. Because the switch 46 is in the "auto" position, the AED 82 turns off automatically in response to the closing of the loop 88, thus eliminating the need for the operator to manually turn the switch 46 to the "off" position.

Other embodiments of the AED system 80 are contemplated as well. For example, the switch 46 may be omitted such that the AED 82 operates only in the automatic mode. Alternatively, one can program the operating mode of the AED 82 via a personal computer and interface (not shown) or via the screen 22. In such embodiments, when the AED 82 is in the automatic mode, one can attach a jumper (not shown) to the end 92 of the line 90 to close the loop 88 and turn the AED off when it is out of the case 84.

Figure 7:
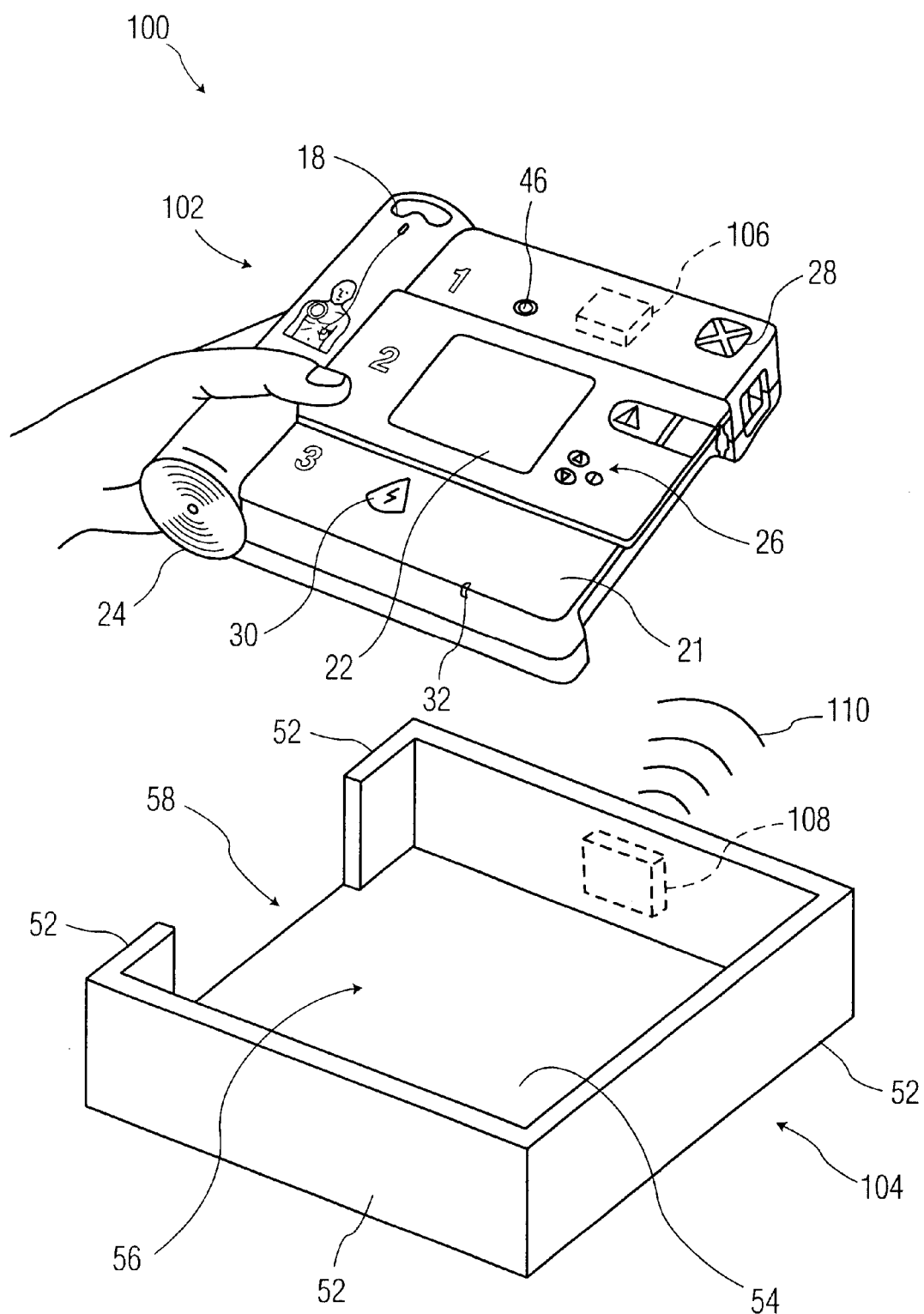
FIG. 7 is a perspective view of an AED system that includes an automatically activating/deactivating AED according to an embodiment of the invention.

FIG. 7 is a perspective view of an AED system 100 that includes an automatically activating/deactivating AED 102 and an AED storage case 104 according to another embodiment of the invention, where like numerals refer to like elements in the systems 40 (FIG. 2) and 100. The AED system 100 of FIG. 7 is the same as the system 40 of FIG. 2 except that the AED 102 includes an activator/deactivator receiver 106 instead of the magnetic activator/deactivator 48, and the case 104 includes a deactivator transmitter 108 instead of the magnetic deactivator element 50. When the switch 46 is in the "auto" position, the receiver 106 deactivates the AED 102 when it receives a predetermined signal 110 from the transmitter 108. Conversely, the receiver 106 activates the AED 102 when it does not receive the predetermined signal 110. Because they can be conventional, a detailed discussion of the receiver 106 and transmitter 108 is omitted for brevity.

Still referring to FIG. 7, the operation of the system 100 in the automatic mode is discussed (in the manual mode, the system 100 operates in a manner similar to that discussed above in conjunction with FIG. 2 for the system 40).

In the automatic mode, the AED 102 is stored in the case 104 with the switch 46 in the "auto" position, which allows the receiver 106 to control the on/off function of the AED.

During a cardiac emergency, an operator (hands shown in FIG. 7) removes the AED 102 from the case 104. Because the switch 46 is in the "auto" position, the AED 102 turns on automatically, thus eliminating the need for the operator to manually turn the switch 46 to the "on" or "auto" position. Specifically, as the AED 102 moves away from the case 104, the receiver 106 senses a weakening of the signal 110. When the strength of the signal 110 falls below a predetermined threshold, the receiver 106 turns on the AED 102. In one embodiment, the sensitivity of the receiver 106 and/or the strength of the signal 110 are set such that the receiver activates the AED 102 when the AED is more than an inch or two from the case 104. Once the AED 102 is activated, the operator sets up the AED and uses the AED to shock a patient (not shown) as discussed above in conjunction with FIG. 1.

After the operator finishes treating the patient with the AED 102, he returns it to the case 104. Because the switch 46 is in the "auto" position, the AED 102 turns off automatically, thus eliminating the need for the operator to manually turn the switch 46 to the "off" position. Specifically, as the AED 102 moves toward the case 104, the receiver 106 senses a strengthening of the signal 110. When the strength of the signal 110 rises above the predetermined threshold, the receiver 106 turns off the AED 42.

Other embodiments of the AED system 100 are contemplated as well. For example, the switch 46 may be omitted such that the AED 102 operates only in the automatic mode. Alternatively, one can program the operating mode of the AED 102 via a personal computer and interface (not shown) or via the screen 22. In such embodiments, when the AED 102 is in the automatic mode, one can attach a transmitter like the transmitter 108 to the AED to turn the AED off when it is out of the case 104. In another example, both the AED 102 and the case 104 include respective transmitter/receivers (not shown) such as those used in highway toll-tag systems. The AED transmitter/receiver polls the case transmitter/receiver, deactivates the AED 102 when it receives a response from the case transmitter/receiver, and activates the AED when it receives no response. In yet another example, the AED 102 includes a transmitter/receiver and the case 104 includes a resonant circuit such as those used in badge-identification systems. The AED transmitter/receiver transmits a range of frequencies that includes the resonant frequency of the case resonant circuit, deactivates the AED if it detects a null at the resonant frequency, and activates the AED if it detects no null.

Figure 8:
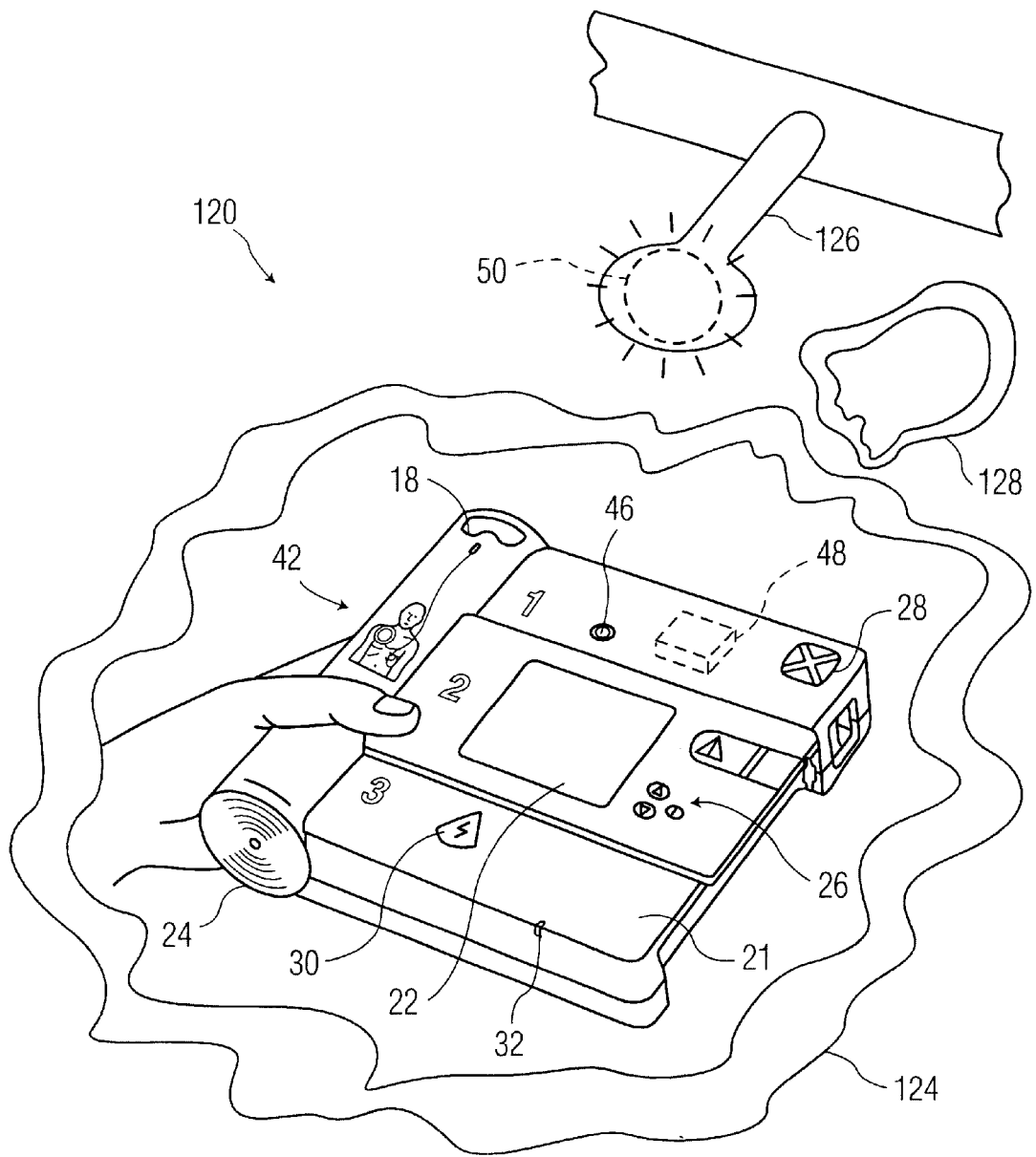
FIG. 8 is a perspective view of an AED system that includes an automatically activating/deactivating AED according to another embodiment of the invention.

FIG. 8 is a perspective view of an AED system 120 that includes the automatically activating/deactivating AED 42 of FIG. 2 according to another embodiment of the invention, where like numerals refer to like elements in the systems 40 (FIG. 2) and 120. The AED system 120 of FIG. 8 is the similar to the system 40 of FIG. 2 except that deactivator element 50 is disposed outside of an AED case 124, such as in a storage peg 126. One stores the AED 42 by hanging a loop 128 over the peg 126. In a related embodiment, the case 124 is omitted and the loop 128 is attached directly to the AED 42.

Figure 9:
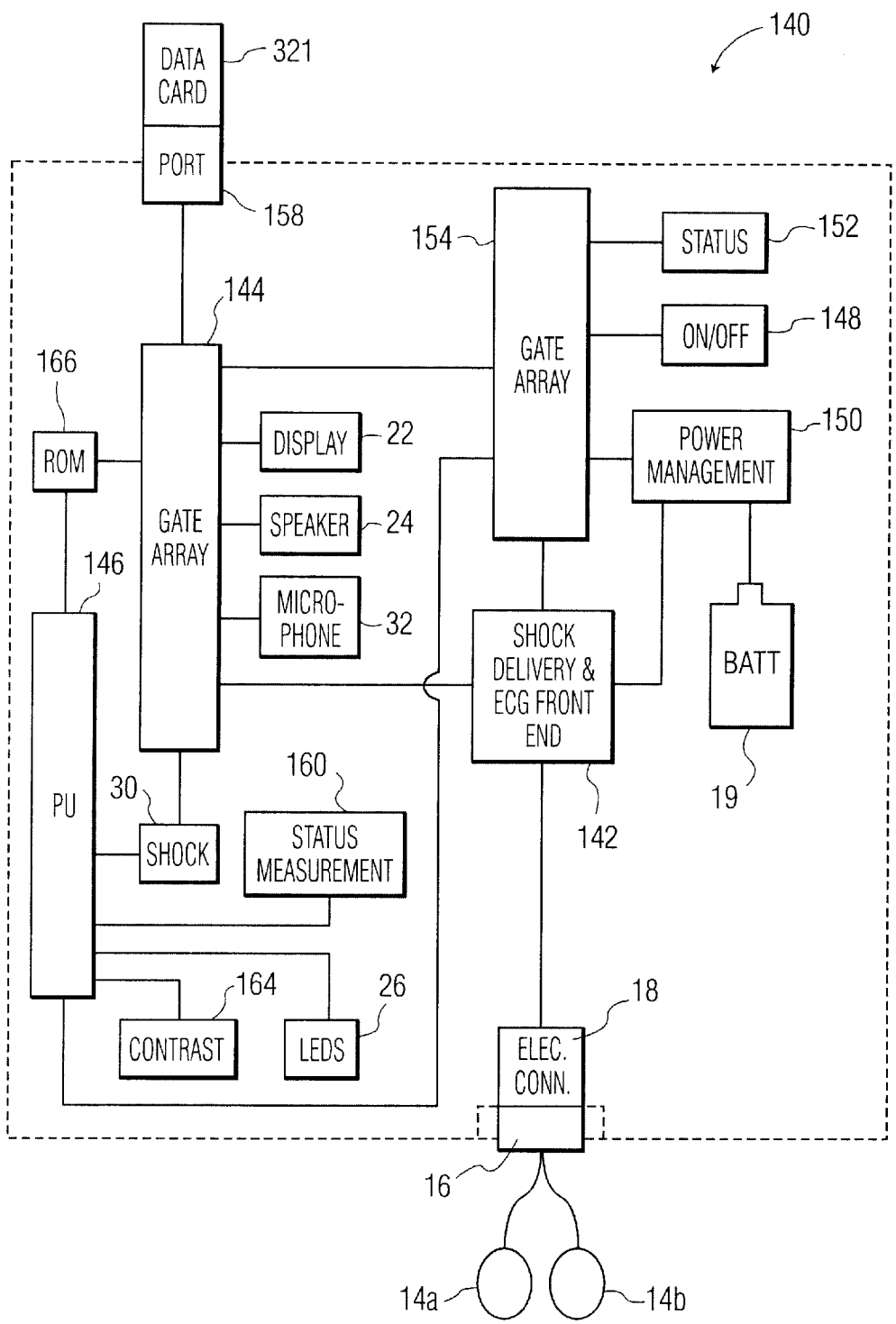
FIG. 9 is a block diagram of an AED circuit that the AEDs of FIGS. 2–4 and 6–8 can incorporate according to an embodiment of the invention.

FIG. 9 is a block diagram of an AED circuit 140, which the AEDs 42 (FIGS. 2, 3, and 8), 62 (FIG. 4), 82 (FIG. 6), and 102 (FIG. 7) can incorporate according to an embodiment of the invention. But for clarity and brevity, the circuit 140 is discussed in conjunction with the AED 42 of FIGS. 2, 3, and 8, it being understood that the discussion also applies to the AEDs 62, 82, and 102.

The electrode pads 14a and 14b are coupled to the circuit 140 via the connectors 16 and 18, and are operable to sense a patient's ECG and to apply an electrical shock to the patient (not shown). A shock-delivery-and-ECG front-end circuit 142 samples the patient's ECG during an analysis mode of operation, and provides a shock to the patient via the connectors 16 and 18 and the electrode pads 14a and 14b during a shock-delivery mode of operation. A gate array 144 receives the ECG samples from the circuit 142 and provides them to a processor unit (PU) 146, which stores and analyzes the samples. If analysis of the patient's ECG indicates that the patient is suffering from a shockable heart rhythm, then the processor unit 146 instructs the circuit 142 via the gate array 144 to enable delivery of a shock to the patient when an operator (not shown in FIG. 9) presses the shock button 30. Conversely, if analysis of the patient's ECG indicates that the patient is not suffering from a shockable heart rhythm, then the processor unit 146 effectively disables the shock button 30 by preventing the circuit 142 from delivering a shock to the patient when the operator presses the shock button.

Still referring to FIG. 9, the circuit 140 includes an on/off circuit 148, which includes the switch 46, activator/deactivator 48, and the deactivator element 50 (e.g., FIG. 2). The circuit 140 also includes a power-management circuit 150 for distributing power from the battery 19 to the subcircuits of the circuit 140. A status circuit 152 indicates the status of the circuit 140, and a gate array 154 interfaces the power-management circuit 148, the on/off circuit 148, and the status circuit 152 to the circuit 142, the processor unit 146, and the gate array 144. As discussed above in conjunction with FIG. 1, the AED 42 may include the display 22, which presents information to an operator, a speaker 24, which may provide audio instructions to the operator, and a microphone 32, which may record the operator's voice and other audible sounds. The data card 34 is connected to the gate array 144 via a port 158. The card 34 may store the operator's voice and other sounds along with the patient's ECG and a record of AED events for later study. A status-measurement circuit 160 provides the status of the circuit 140 subcircuits to the processor unit 146 and to the user via the status indicator 28 (FIGS. 2 and 3), and the LEDs 26 provide status information to the operator such as whether the processor unit 146 has enabled the circuit 142 to deliver a shock to the patient. A contrast control 164 allows the operator to control the contrast of the display screen 22 if present, and a memory such as a read only memory (ROM) 166 stores programming information for the processor unit 146 and the gate arrays 144 and 154.

The AED circuit 140 and other AED circuits are further discussed in the following references, which are incorporated by reference: U.S. Pat. No. 5,836,993, U.S. Pat. No. 5,735,879 entitled ELECTROTHERAPY METHOD AND APPARATUS, U.S. Pat. No. 5,607,454 entitled ELECTROTHERAPY METHOD AND APPARATUS, and U.S. Pat. No. 5,879,374 entitled DEFIBRILLATOR WITH SELF-TEST FEATURES.

What is claimed is:

1. A defibrillator, comprising:
    a housing; and
    an activator disposed in or attached to the housing and operable to activate the defibrillator when the housing moves from a predetermined location.

2. The defibrillator of claim 1 wherein the activator is operable to activate the defibrillator in the absence of a magnetic field.

3. The defibrillator of claim 1 wherein the activator is operable to activate the defibrillator in response to a signal.

4. The defibrillator of claim 1 wherein the activator:
    comprises a receptacle; and
    is operable to activate the defibrillator when the receptacle is empty.

5. The defibrillator of claim 1 wherein the activator:
    comprises a pair of nodes; and
    is operable to activate the defibrillator when the nodes are uncoupled from one another.

6. A defibrillator, comprising:
    a housing;
    a circuit disposed in the housing; and
    an activator disposed in or attached to the housing and operable to activate the circuit when the housing moves from a predetermined location.

7. The defibrillator of claim 6 wherein the circuit comprises a processor.

8. The defibrillator of claim 6 wherein the circuit comprises a shock generator.

9. A defibrillator, comprising:

a housing; and a deactivator disposed or attached to the housing and operable to deactivate the defibrillator when the housing is disposed in a predetermined location.

10. The defibrillator of claim 9 wherein the deactivator is operable to deactivate the defibrillator in the presence of a magnetic field.

11. The defibrillator of claim 9 wherein the deactivator is operable to deactivate the defibrillator in the absence of a signal.

12. The defibrillator of claim 9 wherein the deactivator:

comprises a receptacle; and is operable to deactivate the defibrillator when a predetermined object is disposed within the receptacle.

13. The defibrillator of claim 9 wherein the deactivator:

comprises a pair of nodes; and is operable to deactivate the defibrillator when the nodes are directly coupled together.

14. A defibrillator storage case, comprising:

a storage compartment operable to hold a defibrillator; and a deactivator operable to deactivate the defibrillator while the defibrillator is within the storage compartment.

15. The defibrillator storage case of claim 14, further comprising rigid walls that define the storage compartment.

16. The defibrillator storage case of claim 14, further comprising flexible walls that define the storage compartment.

17. The defibrillator storage case of claim 14 wherein the deactivator comprises a magnet.

18. The defibrillator storage case of claim 14 wherein the deactivator comprises a pin.

19. The defibrillator storage case of claim 14 wherein the deactivator comprises a transmitter.

20. The defibrillator storage case of claim 14 wherein the deactivator comprises a receiver.

21. The defibrillator storage case of claim 14 wherein the deactivator comprises a loop of electrically conductive material.

22. A defibrillator system, comprising:

a defibrillator; and a defibrillator storage case operable to deactivate the defibrillator when the defibrillator is disposed within the storage case.

23. The defibrillator system of claim 22 wherein the defibrillator comprises an automatic or semi-automatic external defibrillator.

24. The defibrillator system of claim 22 wherein the defibrillator is operable to activate when the defibrillator is removed from the defibrillator storage case.

25. The defibrillator system of claim 22 wherein the defibrillator is operable to activate when the defibrillator is a predetermined distance or farther from the defibrillator storage case.

26. The defibrillator system of claim 22 wherein the defibrillator storage case comprises a rigid portion.

27. The defibrillator system of claim 22 wherein the defibrillator storage case comprises a flexible portion.

28. The defibrillator system of claim 22 wherein the defibrillator storage case is operable to deactivate the defibrillator when the defibrillator is less than a predetermined distance away from the defibrillator storage case.

29. The defibrillator system of claim 22 wherein:

defibrillator storage case includes a defibrillator deactivator; and the defibrillator includes a defibrillator activator/deactivator that is operable to activate the defibrillator when the activator/deactivator is a predetermined distance or farther from the deactivator.

30. The defibrillator system of claim 22 wherein:

the defibrillator storage case includes a defibrillator deactivator; and the defibrillator includes a defibrillator activator/deactivator that is operable to deactivate the defibrillator when the activator/deactivator is less than a predetermined distance away from the deactivator.

31. A defibrillator system, comprising:

a defibrillator storage case; and a defibrillator operable to activate when it is a predetermined distance or farther from the defibrillator storage case.

32. The defibrillator system of claim 31 wherein the defibrillator is operable to deactivate when is less than the predetermined distance from the defibrillator storage case.

33. The defibrillator system of claim 31 wherein the defibrillator is operable to deactivate when it is within the defibrillator storage case.

34. A method, comprising:

moving a defibrillator from a location; and activating the defibrillator in response to moving the defibrillator.

35. The method of claim 34 wherein activating the defibrillator comprises activating the defibrillator in response to a decreasing magnetic field.

36. The method of claim 34 wherein activating the defibrillator comprises activating the defibrillator in response to a loss of communication between the defibrillator and a device located at the location.

37. The method of claim 34 wherein activating the defibrillator comprises activating the defibrillator in response to an object being removed from the defibrillator.

38. A method, comprising:

placing a defibrillator into a location; and deactivating the defibrillator in response to placing the defibrillator.

39. The method of claim 38 wherein deactivating the defibrillator comprises deactivating the defibrillator in response to an increasing magnetic field.

40. The method of claim 38 wherein deactivating the defibrillator comprises deactivating the defibrillator in response to a communication between the defibrillator and a device located at the location.

41. The method of claim 38 wherein deactivating the defibrillator comprises deactivating the defibrillator in response to an object being inserted into the defibrillator.

* * * * *